US012458767B2

(12) United States Patent
Baillet et al.

(10) Patent No.: US 12,458,767 B2
(45) Date of Patent: Nov. 4, 2025

(54) DEVICE FOR DISPENSING A FLUID PRODUCT

(71) Applicant: APTAR FRANCE SAS, Le Neubourg (FR)

(72) Inventors: Matthieu Baillet, Rouen (FR); Diego Espinoza, Oissel (FR)

(73) Assignee: APTAR FRANCE SAS, Le Neubourg (FR)

( * ) Notice: Subject to any disclaimer, the term of this patent is extended or adjusted under 35 U.S.C. 154(b) by 847 days.

(21) Appl. No.: 17/775,644

(22) PCT Filed: Nov. 10, 2020

(86) PCT No.: PCT/FR2020/052054
§ 371 (c)(1),
(2) Date: May 10, 2022

(87) PCT Pub. No.: WO2021/094683
PCT Pub. Date: May 20, 2021

(65) Prior Publication Data

US 2022/0409833 A1 Dec. 29, 2022

(30) Foreign Application Priority Data

Nov. 12, 2019 (FR) ...................................... 1912629

(51) Int. Cl.
*A61M 15/08* (2006.01)
*A61M 11/00* (2006.01)
(Continued)

(52) U.S. Cl.
CPC .......... *A61M 15/08* (2013.01); *A61M 11/007* (2014.02); *A61M 15/0036* (2014.02);
(Continued)

(58) Field of Classification Search
CPC ............ A61M 11/007; A61M 15/0041; A61M 15/0036; A61M 15/0028; A61M 15/08; B05B 11/02
See application file for complete search history.

(56) References Cited

U.S. PATENT DOCUMENTS 5,944,222 A * 8/1999 Fuchs ................ B05B 11/0027 222/153.13
6,708,846 B1 * 3/2004 Fuchs ................ B05B 11/1091 222/386
(Continued)

FOREIGN PATENT DOCUMENTS

CA 2653422 A1 * 12/2007 ........ A61M 15/0021
CN 103561873 A * 2/2014 ............... B05B 1/34
(Continued)

OTHER PUBLICATIONS

International Preliminary Report on Patentability dated May 17, 2022 with a Translation of the Written Opinion of the International Searching Authority in Application No. PCT/FR2020/052054.
(Continued)

*Primary Examiner* — Tu A Vo
(74) *Attorney, Agent, or Firm* — Sughrue Mion, PLLC

(57) ABSTRACT

A dispenser including a reservoir (10) containing fluid product, a head (20) provided with an opening (21), a piston (50) for dispensing at least one portion of the fluid product through the opening (21), the reservoir (10) being, before the dispenser is actuated, closed in sealed manner by the piston (50), the device including a hollow insert (60) inserted and fixed in the head (20), the insert (60) supporting a cannula (40) for piercing the piston (50) and thus connecting the container (10) to the opening (21) during actuation, wherein:
the dispenser head (20) includes a proximal end portion (220) of reduced diameter the axial length of which is greater than 5 mm, advantageously greater than 6 mm,
(Continued)

the maximum outside diameter of which is less than 8 mm, advantageously less than 7 mm, and the wall thickness of which is less than 1.1 mm, advantageously between 0.7 and 1.0 mm.

19 Claims, 2 Drawing Sheets

(51) Int. Cl.
*A61M 15/00* (2006.01)
*B05B 11/02* (2023.01)

(52) U.S. Cl.
CPC ......... *A61M 15/0041* (2014.02); *B05B 11/02* (2013.01); *A61M 15/0028* (2013.01)

(56) References Cited

U.S. PATENT DOCUMENTS

2005/0023295 A1* 2/2005 Tempfli ................. B05B 11/061 222/321.9
2005/0029288 A1* 2/2005 Heldt ...................... B05B 11/02 222/83
2009/0159081 A1* 6/2009 Stadelhofer ........... A61M 15/08 128/203.22
2017/0128364 A1* 5/2017 Kamishita ............ A61K 39/145
2017/0136477 A1* 5/2017 Heldt ................ A61M 15/0036
2022/0135261 A1* 5/2022 Eicher ................... A61M 5/285 53/471

FOREIGN PATENT DOCUMENTS

EP 1078694 A2 * 2/2001 ........ A61M 5/31595
EP 1504783 A1 * 2/2005 ........... B65D 81/325
FR 2739294 A1 * 4/1997 ............ A61M 15/08
FR 2847834 A1 * 6/2004 ........ A61M 15/0028
FR 3029810 A1 * 6/2016 ............. B05B 11/02
WO 2014/147329 A1 9/2014
WO WO-2016001601 A1 * 1/2016 ........ A61M 15/0036
WO WO-2019008260 A1 * 1/2019 ............. B05B 11/02

OTHER PUBLICATIONS

International Search Report for PCT/FR2020/052054 dated Feb. 8, 2021.
Written Opinion for PCT/FR2020/052054 dated Feb. 8, 2021.

* cited by examiner

DEVICE FOR DISPENSING A FLUID PRODUCT

CROSS REFERENCE TO RELATED APPLICATIONS

This application is a National Stage of International Application No. PCT/FR2020/052054 filed Nov. 10, 2020, claiming priority based on French Patent Application No. 1912629 filed Nov. 12, 2019.

The present invention relates to a nasal fluid product dispenser device.

More particularly, the present invention relates to a nasal fluid product dispenser device for dispensing a pharmaceutical fluid product to a user via one or more nasal spray(s).

A disadvantage of existing nasal fluid product dispenser devices relates to their compatibility of the dispenser head with different nose morphologies, in particular in children.

Moreover, in this type of nasal device, the spray is generally produced by means of an insert arranged in the dispenser head, upstream from the dispenser orifice. The molding of these parts can generate problems, such as shrinkage. Putting the insert into place, holding it in place, and sealing it in the dispenser head may also turn out to be complex, with the risk of the device malfunctioning. In particular, since the spray profile is defined between the insert and the dispenser head, the properties of the spray may vary from one device to another depending on the assembly conditions.

Figure 2:
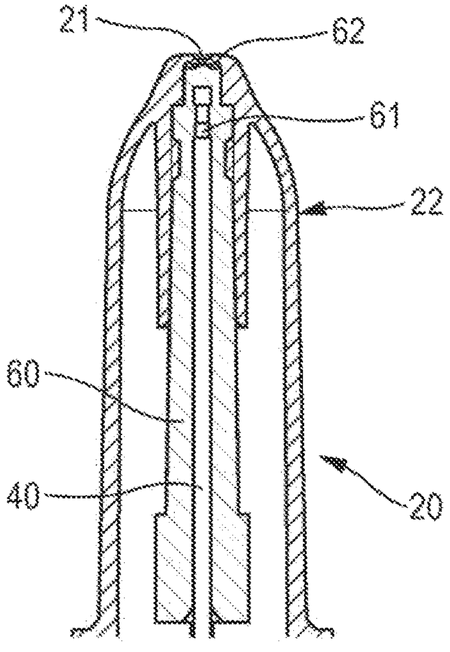

WO2016001601 describes a prior-art device comprising a dispenser head as shown in FIG. 2.

The object of this invention is to provide a fluid product dispenser device that does not have the above mentioned disadvantages.

More particularly, an object of the present invention is to provide a fluid product dispenser device that avoids or limits any risk of malfunction of the device and improves its robustness.

Another object of the present invention is to provide such a device that is simple and inexpensive to manufacture and to assemble.

The present invention thus provides a fluid product dispenser device comprising a reservoir containing fluid product, a dispenser head that is provided with a dispenser orifice, a stopper/piston for dispensing at least a portion of said fluid product through said dispenser orifice, said reservoir being closed in sealed manner by said stopper/piston before actuation, said device comprising a hollow insert inserted and fixed in said dispenser head, said insert supporting a cannula to pierce said stopper/piston and thus connect said reservoir to said dispenser orifice during actuation, wherein:

said dispenser head includes a proximal end portion of reduced diameter the axial length of which is greater than 5 mm, advantageously greater than 6 mm, the maximum outside diameter of which is less than 8 mm, advantageously less than 7 mm, and the wall thickness of which is less than 1.1 mm, advantageously between 0.7 and 1.0 mm;

said dispenser head comprises an inner side wall comprising a first proximal cylindrical section and a second distal cylindrical section of diameter greater than that of said first proximal cylindrical section, said insert comprising on its outer wall a first proximal radial projection extending over the entire periphery, said first proximal radial projection cooperating in a tight and sealed manner with said first proximal cylindrical section, in order to ensure the sealed fixing of said insert in said dispenser head.

Advantageously, said insert, in the assembled state, is in abutment by its front surface with the bottom wall of said dispenser head, said abutment forming the only axial contact between said insert and said dispenser head.

Advantageously, said proximal end portion is slightly conical, said proximal end portion including, at said dispenser orifice, an outside diameter less than 6 mm, advantageously less than 5 mm.

According to a first advantageous variant, said proximal end portion extends over an axial distance L1 of at least 5 mm, preferably 6.15 mm, its outside diameter D1 at its distal end being less than 6 mm, in particular 5.7 mm, and its outside diameter D1' at its proximal end, at said dispenser orifice, being less than 5 mm, in particular 4.6 mm.

According to a second advantageous variant, said proximal end portion extends over an axial distance L1 of at least 5 mm, preferably 12.5 mm, its outside diameter D2 at its distal end being less than 7 mm, in particular 6.6 mm, and its outside diameter D2' at its proximal end, at said dispenser orifice, being less than 5 mm, in particular 4.6 mm.

Advantageously, said insert comprises, on its outer wall, a second distal radial projection, axially separated from said first proximal radial projection, said second proximal radial projection cooperating with said second proximal cylindrical section in order to ensure the guidance of said insert when it is inserted into said dispenser head, and the centering in the assembled position.

Advantageously, said first proximal radial projection has an end surface providing radial clamping, the axial dimension of which is less than 1 mm, advantageously less than 0.7 mm.

Advantageously, said second proximal radial projection has an end surface the axial dimension of which is less than 1 mm, advantageously less than 0.6 mm.

Advantageously, said insert comprises, on its front surface, a spray profile disposed, in the assembled state, directly upstream from said dispenser orifice.

Advantageously, said insert defines an expulsion channel, at least one radial opening allowing the fluid to pass from the expulsion channel to said spray profile, said expulsion channel comprising a proximal channel part, at said radial opening, a central channel part of diameter greater than that of said proximal channel part and connected to the latter by a first radial shoulder, and a distal channel part of diameter greater than that of said central channel part and connected to the latter by a second radial shoulder.

Advantageously, said cannula is force fitted in said central channel portion, and its proximal end comes into abutment against said first radial shoulder.

Advantageously, said reservoir contains a single dose of fluid product, dispensed in a single actuation of the device.

In a variant, said reservoir contains two doses of fluid product, dispensed during two successive actuations of the device.

Figure 1:
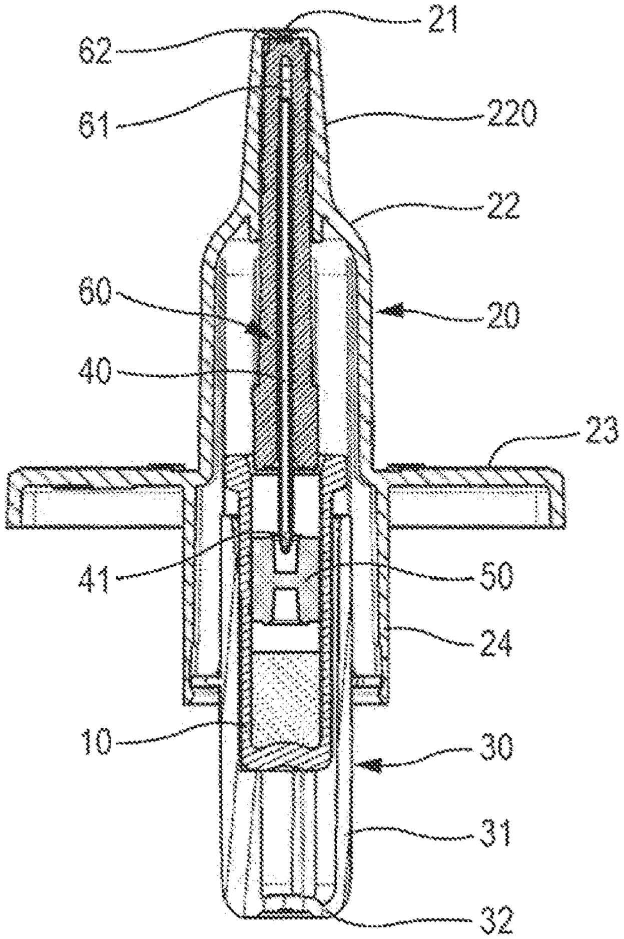
Figure 3:
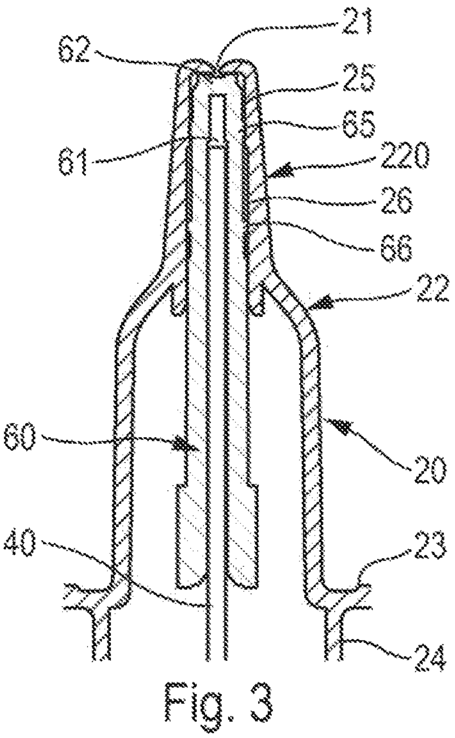
Figure 4:
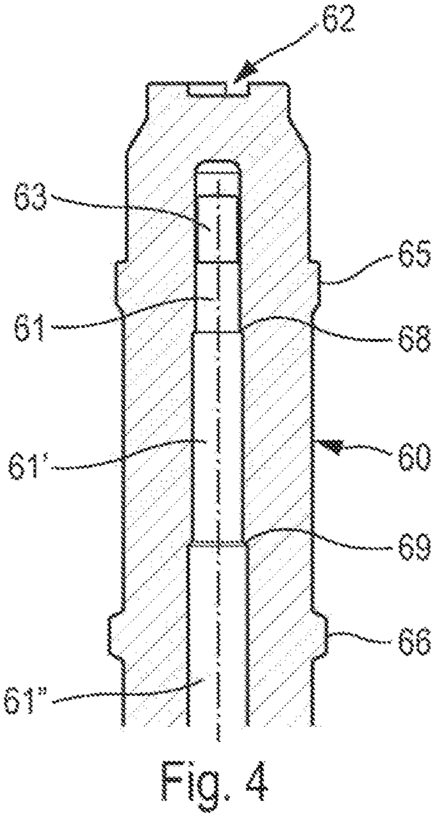
Figure 5:
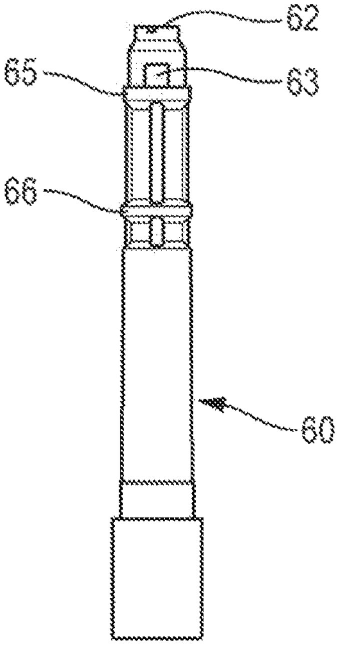
Figure 6A:
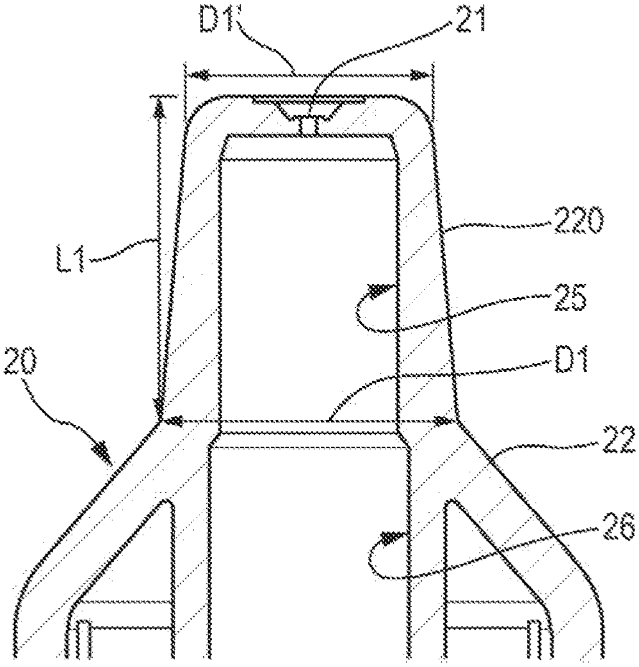
Figure 6B:
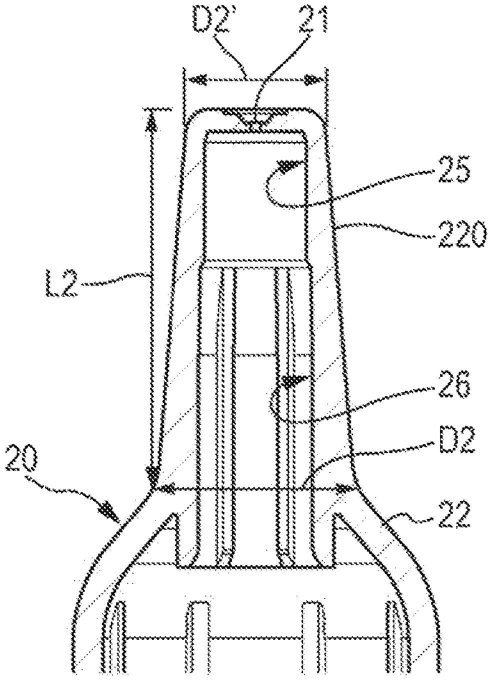

These and other characteristics and advantages of the present invention appear more clearly from the following detailed description, given by way of non-limiting examples, and with reference to the accompanying drawings, and in which:

FIG. 1 is a diagrammatic section view of a fluid product dispenser device in a advantageous embodiment, shown in its rest position before actuation, FIG. 2 is a detail section view of a dispenser head and of an insert of the prior art, FIG. 3 is a view similar to the view in FIG. 2, showing a dispenser head and an insert according to an advantageous embodiment of the present invention, FIG. 4 is a detail section view of the insert of FIG. 3, FIG. 5 is a side view of the insert of FIG. 3, and FIGS. 6*a* and 6*b* are detail section views of two advantageous alternative embodiments of the dispenser head.

The terms "proximal" and "distal" are relative to the dispenser orifice. The terms "axial" and "radial" are relative to the longitudinal central axis of the device. The terms "upstream" and "downstream" are relative to the direction of flow of the fluid during actuation. The terms "top" and "bottom" are relative to the upright position of the device shown in FIG. 1.

With reference to FIGS. 1 and 3 to 5, a advantageous embodiment of the present invention is shown.

In this embodiment, a reservoir 10 containing fluid product to be dispensed, typically a liquid, is arranged inside a body that forms a dispenser head 20. The dispenser head 20 comprises a dispenser orifice 21 oriented axially. The dispenser orifice 21 serves to dispense a dose of fluid out from said dispenser head 20 while the device is being actuated by a user.

The dispenser head 20 comprises a nasal endpiece elongate 22 that, at its proximal axial end, includes said dispenser orifice 2, and a side body 24 that is connected to said nasal endpiece 22 via a radial flange 23. The inner side wall of the nasal endpiece 22 comprises a first proximal cylindrical section 25 and a second distal cylindrical section 26 of diameter greater than that of the first proximal cylindrical section 25.

A hollow insert 60 is arranged in the dispenser head 20, upstream from said dispenser orifice 21, said hollow insert 60 defining an expulsion channel 61, 61', 61" and, in cooperation with the bottom wall of the dispenser head 20, a spray profile 62 directly upstream from said dispenser orifice 21. At least one radial opening 63, arranged in the proximity of the proximal end of the insert 60, allows the fluid to pass from the expulsion channel 61 to the spray profile 62. The expulsion channel comprises a proximal channel part 61, at said radial opening 63. The expulsion channel also includes a central channel portion 61' of diameter greater than that of the proximal channel portion 61 and connected to the latter by a first radial shoulder 68. Finally, the expulsion channel also comprises a distal channel portion 61" of diameter greater than that of the central channel portion 61' and connected to the latter by a second radial shoulder 69. On its outer wall, the insert 60 comprises a first proximal radial projection 65 extending over the entire periphery, as well as a second distal radial projection 66, which may also extend over the entire periphery, and which is axially separated from said first proximal radial projection 65.

A hollow cannula 40 is inserted and fixed in said expulsion channel 61, 61', 61", said cannula 40 comprising a perforator tip 41 at its distal end. Advantageously, said cannula 40 is force-fitted in said central channel portion 61', and its proximal end comes into abutment against said first radial shoulder 68. Thus, the insertion of the cannula 40 into the insert 60 is facilitated, the first radial shoulder 68 defining its assembly position, and the force-fitting being limited to the central channel portion 61'.

In the examples in the Figures, the reservoir 10 is formed by a body that is hollow and blind, including a single opening that is closed by a stopper/piston 50 and containing a single dose of fluid product to be dispensed by a single actuation of the device.

During actuation, the reservoir 10 is displaced axially upwards relative to the dispenser head 20 and thus relative to the cannula 40. The stopper/piston 50 is thus pushed against the tip 41 of the cannula 40 in order to be pierced, which allows all or part of the fluid product contained in the reservoir 10 to be expelled.

It should be observed that the present invention may also be adapted to devices of the dual- or multidose type, wherein the reservoir contains at least one two doses of fluid to be dispensed during two successive actuations of the device.

Actuator means 30 are provided so as to make it possible to actuate the device.

In the embodiment of FIG. 1, the actuator means 30 comprise an actuator body 31 that is movable relative to the dispenser head 20, said actuator body 31 co-operating with said reservoir 10 so as to move it axially relative to the dispenser head 20, towards the dispenser orifice 21.

Operation of the device is described in detail below.

In a conventional manner, the user places two fingers on the radial flange 23 that is formed on the dispenser head 20, and presses with the thumb on the distal axial bottom wall 32 of said actuator body 31. During such actuation, the reservoir 10 is thus pushed axially towards the dispenser orifice 21, so that the cannula 40 pierces the stopper/piston 50. The contents of the reservoir 10 are thus connected to the dispenser orifice 21, and the user pressing on the actuator body 31 moves the stopper 50 in the reservoir 10 so as to dispense the fluid product.

In another embodiment that is not shown in the drawings, the reservoir need not be formed by a hollow and blind body that includes only one opening, but may be formed by a hollow cylinder that is open axially at both ends. The cylinder would thus be closed at the proximal end by a first stopper and at the distal end by a second stopper, the volume defined between said two stoppers containing the fluid to be dispensed. When the user actuates the device, the user presses axially on the actuator body so as to slide it axially towards the dispenser orifice, as described above. This causes the second plug to move inside the reservoir. However, the fluid being incompressible, the movement of the second stopper thus moves the first stopper towards the cannula, which is stationary. The first stopper is thus pierced by the cannula and the contents of the reservoir are dispensed the dispenser orifice, and the second stopper which thus acts as a piston.

As described above, the invention could also apply to a device of the dual-dose type. In that configuration, the contents of the reservoir would be dispensed in two successive actuations. Document WO 2014/147329 describes an example of a dual-dose device.

According to the invention, the dispenser head 20 and the insert 60 have particular shapes and dimensions, which improve the molding and assembly of these parts, as well as the reliability of operation of the device.

The nasal endpiece 22 of the dispenser head 20 includes a proximal end portion 220 of reduced diameter. This proximal end portion 220 is advantageously slightly conical. It has an axial length greater than 5 mm, advantageously greater than 6 mm. It has a maximum outside diameter less than 8 mm, advantageously less than 7 mm. At the level of the dispenser orifice 21, said proximal end portion 220 advantageously has an outside diameter less than 6 mm, advantageously less than 5 mm.

In the variant of FIG. 6*a*, said proximal end portion 220 extends over an axial distance L1 of at least 5 mm, preferably 6.15 mm. Its outside diameter D1 at the distal end is less than 6 mm, preferably 5.7 mm. Its outside diameter D1' at the proximal end, at the dispenser orifice 21, is less than 5 mm, preferably 4.6 mm.

In the variant of FIG. 6*a*, said proximal end portion 220 extends over an axial distance L2 of at least 10 mm, preferably 12.5 mm. Its outside diameter D2 at the distal end is less than 7 mm, preferably 6.6 mm. Its outside diameter D2' at the proximal end, at the dispenser orifice 21, is less than 5 mm, preferably 4.6 mm. The thickness of the wall of said end portion 220 is less than 1.1 mm, advantageously between 0.7 and 1.0 mm. This implementation improves the molding of the dispenser head 20, in particular by reducing the risks of deformation associated with excess thickness and by reducing the risks of shrinkage.

When the insert 60 is assembled in the dispenser head 20, it is inserted therein until the spray profile 62 disposed on the front surface of the insert comes into abutment against the bottom wall of the dispenser head 20. This is the only axial contact between the insert 60 and the dispenser head. There is therefore no longer any double axial contact, as in the device of the prior art shown in FIG. 2, which was capable, in particular because of the manufacturing tolerances of the insert and of the dispenser head, of generating different spray profiles between different devices. With the present invention and its unique axial contact at the spray profile, it is guaranteed that the latter always has the same geometry, with consequently always the same spray properties.

In the assembled position, the first proximal radial projection 65 co-operates in a tight and sealed manner with the first proximal cylindrical section 25 of the nasal endpiece 22, so as to ensure sealed fixing of the insert 60 in the dispenser head 20. The second proximal radial projection 66 co-operates with the second proximal cylindrical section 26 of the nasal endpiece 22. This cooperation ensures that the insert 60 is guided when it is inserted into the dispenser head 20, and that it is centered in the assembled position, and it is therefore neither sealed nor tight.

The first proximal radial projection 65 has an end surface that provides radial clamping with the first proximal cylindrical section 25. The axial dimension of this first proximal radial projection 65 is less than 1 mm, advantageously less than 0.7 mm, preferably 0.63 mm. Thus, since the clamping surface is greatly reduced, the assembly of the insert 60 in the dispenser head is facilitated, requiring a lower insertion force than that of the prior art device of FIG. 2, in which the clamping surface between the insert and the dispenser head is typically greater than 5 mm. The risks of damaging the insert during its assembly are therefore reduced.

The second distal radial projection 66 has an end surface the axial dimension of which is less than 1 mm, advantageously less than 0.6 mm, preferably 0.53 mm. Thus, even in the case of contact between said second distal radial projection 66 and the second distal cylindrical section 26 during assembly, this contact on a surface of small dimension does not alter the assembly process.

The present invention thus provides a device for which the manufacture and assembly of the dispenser head and its insert are simplified, more reliable and less costly, making the device more robust and guaranteeing reproducible performance.

Naturally, other variant embodiments may also be envisaged, without going beyond the ambit of the present invention, as defined by the accompanying claims.

The invention claimed is:

1. A fluid product dispenser device comprising a reservoir containing a fluid product, a dispenser head that is provided with a dispenser orifice, a stopper piston for dispensing at least a portion of said fluid product through said dispenser orifice, said reservoir being closed in sealed manner by said stopper-piston before actuation, said device including a hollow insert that is inserted and fixed in said dispenser head, said insert supporting a cannula for piercing said stopper-piston and thus connecting said reservoir to said dispenser orifice during actuation, said dispenser head includes a proximal end portion of reduced diameter, an axial length of said proximal end portion is greater than 5 mm, a maximum outside diameter of said proximal end portion is less than 8 mm, and a wall thickness of said proximal end portion is less than 1.1 mm;

said dispenser head comprises an inner side wall comprising a first proximal cylindrical section and a second distal cylindrical section comprising a diameter greater than a diameter of said first proximal cylindrical section, said insert comprising on an outer wall of said insert a first proximal radial projection extending over an entire periphery of a circumferential section of said insert, said first proximal radial projection cooperating in a tight and sealed manner with said first proximal cylindrical section, in order to ensure a sealed fixing of said insert in said dispenser head, said insert includes, on an outer wall of said insert, a second distal radial projection, axially separated from said first proximal radial projection, said second distal radial projection co-operating with said second distal cylindrical section to ensure a guidance of said insert when said insert is inserted into said dispenser head, and a centering of said insert in an assembled position of said insert and said dispenser head, wherein said second distal radial projection has an end surface, wherein an axial dimension of the end surface is less than 1 mm.

2. The device according to claim 1, wherein said insert, in the assembled state, abuts with a front surface of said insert against a bottom wall of said dispensing head, said abutment forming the only axial contact between said insert and said dispensing head.

3. The device according to claim 1, wherein said proximal end portion is conical, said proximal end portion having at said dispenser orifice an outside diameter of less than 6 mm.

4. The device according to claim 3, wherein said proximal end portion extends over said axial length of 6.15 mm or at least 5 mm, an outer diameter of said proximal end portion at a distal end of said proximal end portion being 5.7 mm or less than 6 mm, and an outer diameter at a proximal end of said proximal end portion, at said dispenser orifice, being 4.6 mm or less than 5 mm.

5. The device according to claim 3, wherein said proximal end portion extends over said axial length of 12.5 mm or at least 5 mm, an outer diameter of said proximal end portion at a distal end of said proximal end portion being 6.6 mm or less than 7 mm, and an outer diameter at a proximal end of said proximal end portion, at said dispenser orifice, being 4.6 mm or less than 5 mm.

6. The device according to claim 3, wherein said proximal end portion extends over said axial length of at least 5 mm, an outer diameter of said proximal end portion at a distal end of said proximal end portion being less than 6 mm, and an outer diameter at a proximal end of said proximal end portion, at said dispenser orifice, being less than 5 mm.

7. The device according to claim 3, wherein said proximal end portion extends over said axial length of at least 5 mm, an outer diameter of said proximal end portion at a distal end of said proximal end portion being less than 7 mm, and an outer diameter at a proximal end of said proximal end portion, at said dispenser orifice, being less than 5 mm.

8. The device according to claim 1, wherein the axial dimension of the end surface of said second distal radial projection is less than 1 mm.

9. The device according to claim 1, wherein said first proximal radial projection has a radially clamping end surface, an axial dimension of said first proximal radial projection is less than 1 mm.

10. The device according to claim 1, wherein said insert has on a front surface of said insert a spray profile arranged, in the assembled state, directly upstream of the said dispenser orifice.

11. The device according to claim 10, wherein said insert defines an expulsion channel and at least one radial opening allowing the fluid to pass from the expulsion channel to said spray profile, said expulsion channel comprising a proximal channel portion, at said at least one radial opening, a central channel portion comprising a diameter greater than a diameter of said proximal channel portion and said central channel portion connected to said proximal channel portion of said expulsion channel by a first radial shoulder, and said insert defines a distal channel portion comprising a diameter greater than the diameter of said central channel portion and said distal channel portion is connected to the central channel portion by a second radial shoulder.

12. The device according to claim 11, wherein said cannula is force-fitted into said central channel portion, and a proximal end of said cannula abuts said first radial shoulder.

13. The device according to claim 1, wherein said reservoir contains a single dose of fluid dispensed in a single actuation of the device.

14. The device according to claim 1, wherein said reservoir contains two doses of fluid dispensed in two successive actuations of the device.

15. The device according to claim 1, wherein the axial length of said proximal end portion is greater than 6 mm.

16. The device according to claim 1, wherein the maximum outside diameter of said proximal end portion is less than 7 mm.

17. The device according to claim 1, wherein and the wall thickness of said proximal end portion is between 0.7 and 1.0 mm.

18. The device according to claim 1, wherein the axial dimension of the end surface of said second distal radial projection is less than 0.6 mm.

19. The device according to claim 1, wherein said first proximal radial projection has a radially clamping end surface, an axial dimension of said first proximal radial projection is less than 0.7 mm.

* * * * *